United States Patent [19]
Roy et al.

[11] Patent Number: 5,292,407
[45] Date of Patent: Mar. 8, 1994

[54] PROCESS FOR CONVERTING HEAT STABLE AMINE SALTS TO HEAT REGENERABLE AMINE SALTS

[75] Inventors: Veronique Roy, Laval; Leo E. Hakka, Dollard des Ormeaux; Jean I. Sarlis, Laval, all of Canada

[73] Assignee: Union Carbide Chemicals & Plastics Technology Corporation, Danbury, Conn.

[21] Appl. No.: 993,015

[22] Filed: Dec. 18, 1992

[51] Int. Cl.$^5$ .............................................. B01D 61/44
[52] U.S. Cl. ..................... 204/101; 204/102; 204/131; 204/182.4
[58] Field of Search ................... 204/182.3, 182.4, 101, 204/102, 131

[56] References Cited

U.S. PATENT DOCUMENTS

| 2,797,188 | 6/1957 | Taylor, Jr. et al. | 196/32 |
| 3,554,691 | 6/1981 | Kuo et al. | 23/2 |
| 4,107,015 | 8/1978 | Chlanda et al. | 204/180 |
| 4,389,383 | 6/1983 | Sokolik, Jr. et al. | 423/243 |
| 4,704,463 | 11/1987 | Blytas | 549/521 |
| 4,802,966 | 2/1989 | Aoki et al. | 204/182.4 |
| 4,820,391 | 4/1989 | Walker | 204/182.4 |
| 5,019,361 | 5/1991 | Hakka | 423/243 |

Primary Examiner—John Niebling
Assistant Examiner—Arun S. Phasge
Attorney, Agent, or Firm—W. K. Volles

[57] ABSTRACT

Processes are disclosed for converting heat stable amine salts to heat regenerable amine salts using a modified electrodialysis zone. The processes of the present invention can be used to reduce the level of heat stable salts in a lean solvent stream in an acid gas removal process and can be integrated with the acid gas removal process to utilize process streams as a source of ions.

18 Claims, 1 Drawing Sheet

PROCESS FOR CONVERTING HEAT STABLE AMINE SALTS TO HEAT REGENERABLE AMINE SALTS

FIELD OF THE INVENTION

The present invention relates to the removal of heat stable amine amine salts from liquid streams. More specifically, the present invention relates to processes for converting an amine in salt form having heat stable anions associated therewith to an amine in salt form having heat regenerable anions associated therewith using a modified electrodialysis zone.

BACKGROUND OF THE INVENTION

A wide variety of absorption processes have been proposed for removing acid gases such as, for example, carbon dioxide, hydrogen sulfide, sulfur dioxide, sulfur trioxide, carbon disulfide, hydrogen cyanide, and carbonyl sulfide from process gas streams using absorbents comprising amines.

Such absorption processes typically involve passing the process gas stream containing one or more of the acid gases to an absorption zone wherein it is contacted with a lean solvent comprising the amine absorbent. A product gas stream, depleted in the acid gases relative to the process gas stream, is withdrawn from the absorption zone as a product. A rich solvent stream comprising the amine absorbent and the absorbed acid gases is also withdrawn from the absorption zone and passed to a regeneration zone, e.g., a steam stripping column, wherein the absorbed acid gases are desorbed from the solvent to provide a tail gas stream comprising the acid gases and the lean solvent stream hereinbefore described.

A common problem in such acid gas absorption processes is that heat stable salts of the amine are often formed during one or both of the absorption and regeneration steps as a by-product. Heat stable salts can be formed, for example, when strong acids such as hydrochloric acid or sulfuric acid are present in the process gas. Heat stable salts can also be formed when sulfite anions are oxidized to sulfate anions. Typical ions which form heat stable salts, i.e., heat stable anions, include, for example, sulfate anions, thiosulfate anions, polythionate anions, thiocyanate ions, acetate ions, formate ions and oxylate ions.

Heat stable salts generally do not have absorption capacity for the acid gases and are not regenerable under the conditions of the process. Therefore, the level of heat stable salts needs to be controlled in order to retain an adequate degree of absorption capacity for the acid gases.

Electrodialysis has been proposed as a method for removing heat stable salts from amine containing streams. In a typical electrodialysis process, caustic, e.g., sodium hydroxide, is added to the stream containing the heat stable amine salt in order to dissociate the heat stable anion from the heat stable salt and provide an amine in free base form and a simple heat stable salt, e.g., sodium sulfate. The simple salt is then separated by electrodialysis wherein the charged ions permeate through anion- and cation-selective membranes. The amine, which is non-ionic, does not permeate through the membranes and is discharged from the electrodialysis zone as a product. Often, conventional electrodialysis processes operate in a batch mode wherein the process streams are recirculated until the desired amount of heat stable salts is removed.

Certain problems can result from the use of electrodialysis processes such as described above. For example, since the amine product from the electrodialysis zone is provided in free base form, it can have excessive volatility which can lead to solvent losses during absorption. In addition, since the process is a batch process, the pH and ionic strength within the compartments of the electrolysis zone vary with the discontinuous operation. As a result, the membranes in the electrodialysis zone often experience shrinking and swelling and, ultimately, are subject to mechanical failure. Moreover, to the extent that the amine is not converted to free base form in the caustic treatment step, there can be substantial losses of the amine due to permeation through the membranes in the electrodialysis zone. In addition, conventional electrodialysis requires a source of caustic.

SUMMARY OF THE INVENTION

In accordance with the present invention, processes are provided which utilize a modified electrodialysis zone in order to convert heat stable salts to heat regenerable salts wherein the amine is in salt form associated with regenerable anions. The process of the present invention can provide a high degree of recovery of the amine in the electrodialysis zone, does not require caustic addition and can be highly integrated with acid gas absorption processes in order to permit the use of process streams for ion exchange with the heat stable salts.

More specifically, the present invention provides a process for converting heat stable amine salts to heat regenerable amine salts which comprises:

(a) passing a feedstream comprising an amine in salt form having heat stable anions associated therewith to an electrodialysis zone having a cathode compartment, an anode compartment and at least one repeat unit comprising a reflux compartment disposed between the cathode compartment and the anode compartment, a product compartment disposed between the reflux compartment and the anode compartment, a feed compartment disposed between the product compartment and the anode compartment, and an acid compartment disposed between the feed compartment and the anode compartment, said regenerated solvent stream being passed to the feed compartment;

(b) passing a reflux stream comprising a salt or acid of a heat regenerable anion to the reflux compartment;

(c) passing a direct current potential transversely across each compartment, said current being effective to cause: (1) amine cations to dissociate from the heat stable amine salts in the feed compartment and pass into the product compartment; (2) heat regenerable anions to dissociate from the salt or acid in the reflux compartment and pass into the product compartment; and (3) heat stable anions to dissociate from the heat stable amine salts in the feed compartment and pass into the acid compartment; and (d) discharging from the product compartment a product stream comprising an amine in salt form having heat regenerable anions associated therewith.

DETAILED DESCRIPTION OF THE INVENTION

Figure 1:
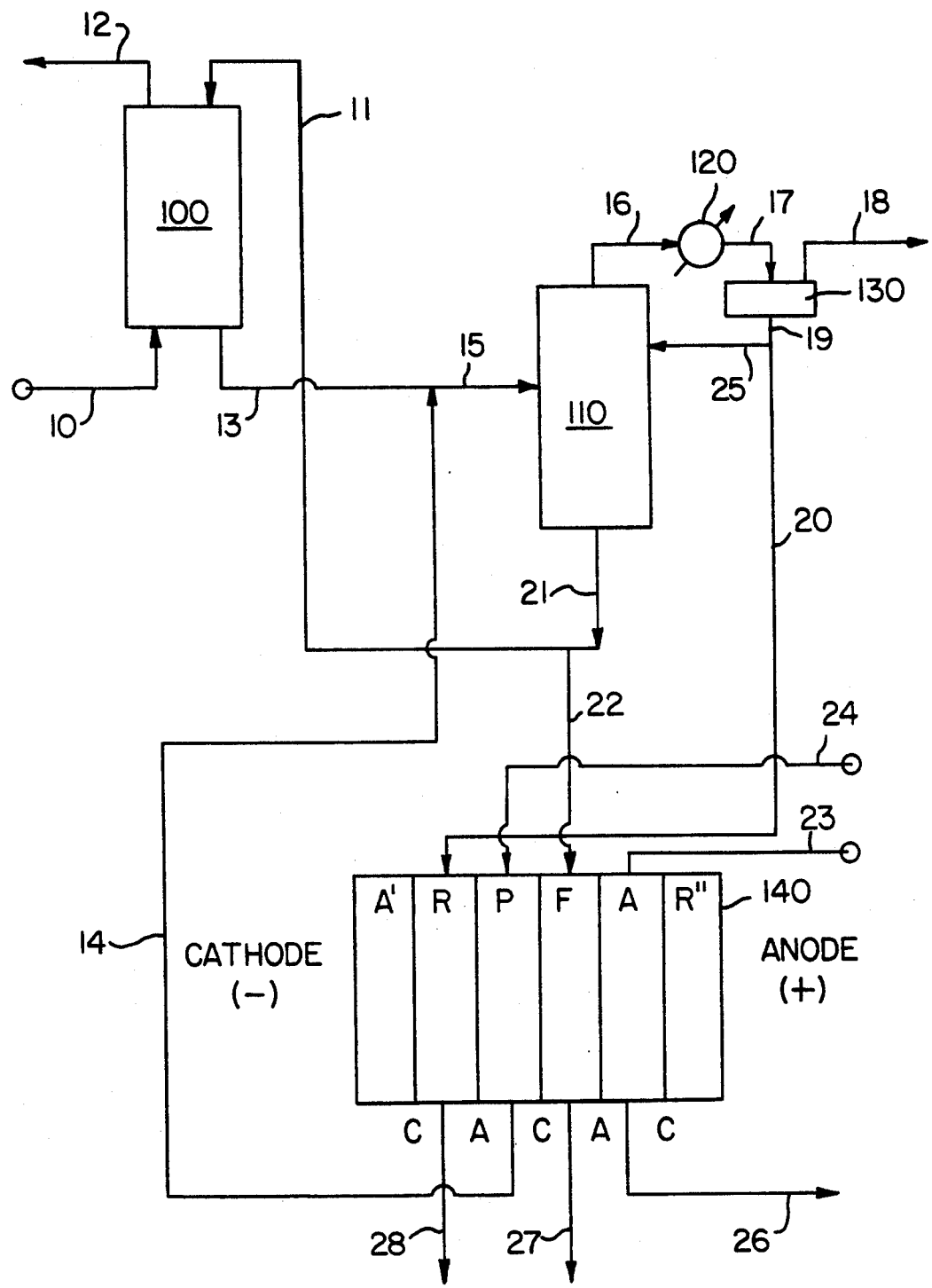
FIG. 1 illustrates a process flow diagram in accordance with the present invention wherein a heat stable amine salt is converted to an amine sulfite salt.

Feedstreams suitable for use in accordance with the present invention generally include any liquid stream comprising an amine in a salt form having heat stable anions associated therewith. Typically, the feedstreams are aqueous and also comprise an amine in free base form. The concentration of the heat stable amine salt is typically from about 0.1 to 25 weight percent based on the total feedstream. In hydrogen sulfide and carbon dioxide acid gas absorption processes, for example, the concentration of heat stable amine salts is often from about 1 to 5 weight percent. In sulfur dioxide acid gas absorption processes, for example, the concentration of heat stable amine salts is often from about 4 to 15 weight percent. The concentration of amine in free base form, when present, is typically from about 5 to 60 weight percent, more typically from about 20 to 50 weight percent, and often from about 25 to 45 weight percent, based on the total feedstream. The concentration of water, when present, typically comprises the balance of the feedstream and is preferably from about 30 to 95 weight percent, and, more preferably, from about 40 to 70 weight percent, based on the total feedstream. It is not uncommon for the feedstreams to comprise small amounts, e.g., less than about 2 weight percent, of other ingredients, such as, for examples, antifoams or antioxidants.

The source of the feedstreams is typically from the solvent circulation loop of an acid gas absorption process. Often, the feedstream comprises a slip stream of the lean solvent stream, i.e., regenerated solvent, from a regeneration zone, e.g., steam stripping column, of an acid gas absorption process such as described above. However, it is to be understood that the source of the feedstream is not a critical aspect of the present invention. In addition, the particular acid gas being absorbed in the acid gas absorption process is not a critical aspect of the present invention. Typical acid gases include hydrogen sulfide, and carbon dioxide. When hydrogen sulfide is present in the process gas stream, its concentration typically ranges from about 10 to 50,000 parts per million volume ("ppmv") or even up to about 30 volume percent or more. When carbon dioxide is present in the process gas stream, its concentration typically ranges from about 2 to 30 volume percent, although levels of carbon dioxide as high as about 90 volume percent or more are not uncommon. When sulfur oxides are present in the process gas stream, i.e., sulfur dioxide and/or sulfur trioxide, their total concentration typically ranges from about 500 to 200,000 ppmv. The process gas streams typically comprise other ingredients such as, for example, nitrogen, water, oxygen, light hydrocarbons in the $C_1$ to $C_4$ range and sulfur derivatives of light hydrocarbons, e.g., $C_1$ to $C_4$ mercaptans.

The processes of the present invention can be used to treat feedstreams containing essentially any amine which can exist in a salt form having heat stable anions associated therewith. Suitable amines include, for example, aliphatic, aromatic and heterocyclic amines in primary, secondary or tertiary configurations. Typical alkanol amines suitable for use in accordance with the present invention include monoethanolamine, diethanolamine, triethanolamine, diisopropanolamine and methyldiethanolamine, for example. Typical alkyleneamines include, for example, ethylene diamine and alkyl derivatives thereof. Typical aromatic amines include, for example, aniline and xylidine. Typical heterocyclic amines include, for example, piperazine and derivatives thereof.

Preferred amines for use in accordance with the present invention for absorbing hydrogen sulfide and carbon dioxide are monoamines. Examples of suitable monoamines include, for example, monoethanolamine, diethanolamine, triethanolamine, methyldiethanolamine, dimethylethanolamine, monoisopropanolamine, diisopropanolamine and diglycolamine.

Preferred amines for use in accordance with the present invention for sulfur dioxide absorption are diamines. In free amine form the diamine can be represented by the structural formula:

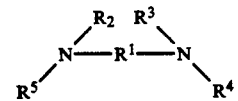

wherein $R^1$ is alkylene of two or three carbon atoms, $R^2$, $R^3$, $R^4$, and $R^5$ may be the same or different and can be hydrogen, alkyl (e.g., lower alkyl of 1 to about 8 carbon atoms including cycloalkyls), hydroxyalkyl (e.g., lower hydroxy alkyl of 2 to about 8 carbon atoms), aralkyl (e.g., 7 to about 20 carbon atoms), aryl (often monocyclic or bicyclic), alkaryl (e.g., 7 to about 20 carbon atoms), and any of $R^2$, $R^3$, $R^4$, and $R^5$ may form cyclic structures. The diamines preferably are tertiary diamines, in view of their stability. However, other diamines in which one or both of the nitrogens is primary or secondary may be employed, provided mild oxidative or thermal conditions exist to minimize chemical reaction of the absorbent. Often, the preferred diamines have a hydroxyalkyl group as a substituent on an amine group. Those skilled in the art will recognize that although diamines are specifically described herein, polyamines, i.e., containing more than two amine groups are also intended to be included within the scope of the invention.

When the amine is used in an acid gas absorption process for absorbing sulfur dioxide, it is preferable for the free amine form of the diamine to have a molecular weight less than about 300, preferably less than about 250. Often the tertiary diamines are of the formula:

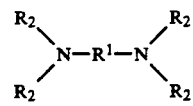

wherein $R_1$ is an alkylene group, preferably containing from 2 to 3 carbon atoms as a straight chain or as a branched chain, and each $R_2$ is the same or different and is an alkyl group, preferably methyl or ethyl, or a hydroxy-alkyl group, preferably 2-hydroxyethyl.

Preferably, the pKa value of the first amine group, i.e., stronger amine, of the diamine is from about 8.0 to 10.6. Preferably, the pKa value of the second amine group, i.e., weaker nitrogen, is from about 4.5 to 7.3. Since the pKa of an amine varies with temperature, for the sake of uniformity all pKa values referred to herein are those measured at 25° C. Examples of preferred diamines in free base form include:
N,N',N'-(trimethyl)-N-(2-hydroxyethyl)-ethylenediamine, N,N,N',N'-tetramethyl-ethylenediamine, N,N,N',N'-tetramethyl-diaminomethane, N,N,N',N'- tetrakis-(2-hydroxyethyl)-ethylenediamine, N,N'-dimethylpiperazine, N,N,N',N'-tetrakis-(2-hydroxyethyl)-1,3-diaminopropane, N',N'-dimethyl-N, N-bis(2-hydroxyethyl)-ethylenediamine, N-methyl,N'-(2-hydroxyethyl)-piperazine, N-(2-hydroxyethyl)-piperazine, N,N'-bis (2-hydroxyethyl)-piperazine, N-methylpiperazine, and piperazine. Mixtures of such amines are also preferred. Especially preferred amines include N,N',N'-(trimethyl)-N-(2-hydroxyethyl)-ethylenediamine, N-methyl,N'-(2-hydroxyethyl)-piperazine, N-(2-hydroxyethyl)-piperazine, and N,N'-bis(2-hydroxyethyl)-piperazine.

As noted above, heat stable salts often form during absorption or regeneration in acid gas absorption processes. As used herein, the term "heat stable salts" means any amine salt which is not regenerated under the regeneration conditions of the process. For example, typical conditions for regenerating the amine include steam stripping in a distillation column at a temperature of from about 150° to 300° F. and at a pressure of about 0.3 to 2 atmospheres. Heat stable salts are also known to those skilled in the art as those salts whose anions correspond to nonvolatile or strong acids relative to the strength of the amine. Those skilled in the art can determine which anions can form heat stable salts depending on the particular amine and acid gas. Typical ions which form heat stable salts, i.e., heat stable anions, include, for example, sulfate anions, thiosulfate anions, thiocyanate anions, halide anions, nitrate anions, nitrite anions, polythionate anions, acetate anions, formate anions, oxylate anions and mixtures thereof. Even sulfite anions, defined below, which are often heat regenerable anions can be heat stable, for example, when present in a hydrogen sulfide or carbon dioxide absorption process using a monoamine.

In accordance with the present invention, a modified electrodialysis zone is utilized to convert an amine in a salt form having heat stable anions (such as described above) associated therewith to an amine in a salt form having heat regenerable anions associated therewith. Typical ions which form heat regenerable amine salts, i.e., heat regenerable anions, include, for example, sulfite anions, sulfide anions, hydrosulfide anions and carbonate anions.

As used herein, the term "sulfite anions" means sulfite anions as $SO_3^{-2}$, bisulfite anions as $HSO_3^{-}$, or disulfite anions (also known as pyrosulfite anions) as $S_2O_5^{-2}$ and the term "carbonate anions" means carbonate anions as $CO_3^{-2}$ and bicarbonate anions as $HCO_3^{-}$. This conversion of heat stable anions is achieved by modifying the arrangement of the compartments in the electrodialysis zone in order to permit amine cations to pass into a compartment containing the regenerable anions.

The electrodialysis zone comprises a cathode compartment which attracts cations, an anode compartment which attracts anions and at least one repeat unit which contains a reflux compartment, a product compartment, a feed compartment and an acid compartment. The reflux compartment is disposed between the cathode compartment and the anode compartment. The product compartment is disposed between the reflux compartment and the anode compartment. The feed compartment is disposed between the product compartment and the anode compartment. the acid compartment is disposed between the feed compartment and the anode compartment.

Each compartment in the repeat unit is separated by a membrane. The reflux compartment and product compartment are separated by an anionic selective membrane. The product compartment and the feed compartment are separated by a cationic selective membrane. The feed compartment and the acid compartment are separated by an anionic selective membrane. The acid compartment and the reflux compartment of an adjacent repeat unit are separated by a cationic selective membrane. As used herein, the term "cationic selective membrane" means a membrane which will selectively permeate cations over anions. As used herein, the term "anionic selective membrane" means a membrane which will selectively permeate anions over cations. In general, details concerning such membranes are known in the art. However, preferred membranes include those which are polyvinylchloride-based. Examples of preferred cationic selective membranes include Neosepta CM2 and CMX membranes available from Tokuyama Soda Co., Ltd., Tokyo, Japan. Examples of preferred anionic selective membranes include Neosepta AM3 and AMX membranes, also available from Tokuyama Soda Co., Ltd.

Typically, the electrodialysis zone will contain from about 10 to 500 repeat units, and preferably will contain from about 40 to 200 repeat units. The process streams generally flow through the compartments in a co-current direction relative to each other. Also the inlets and outlets of common compartments, e.g., product compartments, are typically connected by a common manifold system. Further details concerning operating conditions and the design of electrodialysis zones are known to those skilled in the art.

In the operation of the electrodialysis zone, the feedstream is passed to the feed compartment wherein amine cations dissociate from the heat stable anions. The amine cations permeate through the cationic selective membrane to the product compartment. The heat stable anions permeate through the anionic selective membrane to the acid compartment. A feed effluent stream, having substantially the same composition as the feedstream except for a reduced concentration of heat stable salts, is discharged from the feed compartment.

A reflux stream comprising the salt or acid of a heat regenerable anion is introduced to the reflux compartment wherein the cation of the salt or acid dissociates from the heat regenerable anion and permeates through the cationic selective membrane to the adjacent acid compartment. The heat regenerable anions permeate through the anionic selective membrane and pass into the product compartment. Typical salts of heat regenerable anions include alkali metal sulfites, alkali metal carbonates, alkaline earth metal sulfites, alkaline earth metal carbonates and mixtures thereof. Preferred salts of heat regenerable anions include sodium carbonate, sodium sulfite, potassium carbonate, sodium sulfide, sodium hydrosulfide, magnesium carbonate, magnesium sulfite, and potassium sulfite. Typical acids of heat regenerable anions include sulfurous acid, carbonic acid and hydrogen sulfide. A preferred source for the acid of a heat regenerable anion is from the overhead of a distillation column in a regeneration zone of an acid gas absorption process. Such streams often contain one or more of the above described acids. A reflux effluent stream having essentially the same composition as the reflux stream, except for a reduced acid concentration, is discharged from the reflux compartment.

A product stream comprising the amine in a salt form having heat regenerable anions associated therewith is discharged from the product compartment. Typically, a carrier stream, preferably an aqueous carrier, is introduced to the product compartment to control the flow rate and concentration of heat regenerable salt in the product stream. Quite advantageously, in accordance with the present invention, the amine contained in the product stream is substantially nonvolatile because it is in salt form. Even though the amine is in salt form, it can be useful as an absorbent if the heat regenerable anion is a weaker anion than the anion being absorbed in the acid gas absorption process. For example, in absorption of sulfur dioxide both sulfite and carbonate anions are suitable for use as the heat regenerable anion. Amine sulfites have absorption capacity for sulfur dioxide via the sulfite/bisulfite absorption cycle. When carbonate anions are employed, they will be readily displaced in the absorption zone by sulfite anions which form when sulfur dioxide is absorbed from the process gas stream. The sulfite anions are stronger anions than the carbonate anions. Absorption of additional sulfur dioxide can then proceed via the sulfite/bisulfite absorption cycle. In hydrogen sulfide absorption processes, sulfide anions, hydrosulfide anions and carbonate anions are suitable for use as the heat regenerable anion.

An acid stream comprising the salt or acid of the heat stable anion is discharged from the acid compartment. Typical salts of the heat stable anions include, for example, alkali metal sulfates, alkali metal halides, alkaline earth metal sulfates, alkaline earth metal halides, alkali metal nitrates and nitrites, alkaline earth metal nitrates and nitrites, alkali metal acetates, alkaline earth metal acetates, alkali metal thiocyanatates, alkaline earth metal thiocyanates, alkali metal thiosulfates and alkaline earth metal thiosulfates and mixtures thereof. Preferred salts of heat stable anions include sodium sulfate, sodium chloride, sodium acetate, sodium thiocyanate and sodium thiosulfate. Preferably, the salts are soluble in the said stream and do not precipitate out of solution. Such precipitation could adversely affect the operation of the electrodialysis zone. Typical acids of the heat stable anions include, for example, sulfuric acid, hydrochloric acid, hydrofluoric acid, nitric acid, nitrous acid, and acetic acid. A carrier stream, preferably an aqueous carrier, is introduced to the acid compartment in order to control the flow rate of the acid stream and the concentration of acid in the acid stream. The acid stream can be removed from the process as a product, or, alternatively, can be used in the acid gas absorption process, e.g., as a prewashing liquid to remove particulates and heavy metals.

The feedstream and reflux stream can be introduced to the electrodialysis zone on a once-through basis or a recycle basis. When the electrodialysis zone is operated on a recycle basis, a portion of the feed effluent stream and the reflux effluent stream is recycled back to the feed compartment and reflux compartment, respectively. Methods for recycling such streams are generally known to those skilled in the art. Typically, however, holding tanks are employed whereby the feedstream and reflux stream are introduced to their respective holding tanks. The streams then actually introduced to the feed compartment and reflux compartment are obtained from the holding tanks. Likewise, the feed effluent stream and reflux effluent stream are introduced to the respective holding tanks. By operating in this fashion, it is possible to maintain essentially any desired flow rates within the compartments in the electrodialysis zone even though the actual flow rates of the feedstream and reflux stream to the holding tanks may be substantially lower. Effluent streams are then withdrawn from the holding tanks at flow rates which are equivalent to the flow rates of the feedstream and reflux stream in order to maintain steady state concentrations.

In accordance with the present invention, it is possible to maintain the level of heat stable salts in the lean solvent feed to an absorption zone of an acid gas absorption process at a level low enough to not substantially interfere with the absorption of the acid gas.

When the absorbent comprises a monoamine, such as for absorption of hydrogen sulfide and carbon dioxide, the level of heat stable salts in the regenerated absorbent is preferably less than about 0.25 equivalent of heat stable salt per mole of amine, and more preferably less than about 0.10 equivalent per mole of amine.

When the absorbent comprises a diamine, such as for sulfur dioxide absorption, the level of heat stable salts in the regenerated absorbent is typically less than about 1 equivalent of heat stable salt per mole of diamine, preferably less than about 0.8 equivalent per mole of diamine and, more preferably, from about 0.1 to 0.6 equivalent per mole of diamine in order to provide absorption capacity to the first amine group in salt form. In addition, it is preferred that at least about 20 percent, on average, of the first amine groups in salt form be associated with heat regenerable anions, e.g., sulfite anions, and, more preferably, at least about 50 percent, on average, of the first amine groups in salt form being associated with heat regenerable amine.

Quite surprisingly, the recovery of amine in the process of the present invention is very high. Typically, the recovery of amine is at least 80 percent, preferably at least 90 percent, more preferably at least 95 percent, and most preferably at least 99 percent. The recovery can be readily determined by dividing the total amount of amine (both in free base and salt form) introduced to the feed compartment less any amine lost in an effluent from the acid compartment by the amount of amine introduced to the feed compartment. Without being bound to any particular theory, it is believed that the high recovery is due to the arrangement of the compartments within the electrodialysis zone. In the present invention, the amine cations are substantially only able to permeate through the cationic selective membrane between the feed and product compartments. Since the reflux compartment is separated from the product compartment by an anionic selective membrane, very little amine cation, e.g., typically less than about 2 percent, is allowed to permeate to the reflux compartment. In contrast, in a typical electrodialysis process, any amine cations remaining as a result of incomplete caustic treatment will readily permeate through the same cationic selective membrane as the simple salt cations and be lost with the by-product. In addition, the neutral amines can permeate in both directions due to osmotic diffusion and can be physically carried with water which transports the simple salt ions. Thus, the recovery of amine in accordance with the present invention can be substantially higher than the amine recovery in a conventional electrodialysis process.

FIG. 1 illustrates a process flow diagram in accordance with the present invention. The process flow diagram is provided for illustrative purposes and are not intended to limit the scope of the claims which follow. Those skilled in the art will recognize that the process flow diagram does not illustrate various common pieces of process equipment such as, for example, heat exchangers, pumps, compressors, distillation columns, heaters, process control systems and the like.

FIGURE 1

FIG. 1 illustrates an aspect of the invention where a heat stable amine salt, i.e., chloride salt, is converted to a heat regenerable amine salt, i.e., carbonate salt, in the electrodialysis zone.

A process gas stream comprising about 500 ppmv hydrogen sulfide, 10 mole percent carbon dioxide, 5 mole percent water, 1 mole percent hydrochloric acid with the balance comprising methane and nitrogen, is introduced to the process via line 10 and passed to an absorption zone 100. In absorption zone 100, the feed process stream is contacted with a lean solvent stream via line 11, the source of which is hereinafter defined, comprising about 30 weight percent methyldiethanolamine, with the balance being mostly water. The lean solvent stream also contains an antifoam and a corrosion inhibitor. The liquid-to-gas feed ratio ("L/G") is at least 1.5 gallons of lean solvent per 1000 standard cubic feet of process gas. Absorption zone 100 is maintained at a temperature of from about 100° to 160° F. and a pressure of about 200 psia and comprises a packed tower scrubber, the details of which are known to those skilled in the art. The particular absorption apparatus is not critical to the present invention. During absorption of hydrogen sulfide, heat stable salts of the amine, i.e., having chloride anions associated therewith, are formed.

A product gas stream at least partially depleted in hydrogen sulfide relative to the feed gas steam is discharged from absorption zone 100 via line 12.

A rich solvent stream comprising absorbed hydrogen sulfide and the amine is discharged from absorption zone 100 via line 13, combined with a treated solvent stream in a line 14, the source of which is hereinafter defined, and passed to a regeneration zone 110 via line 15. During regeneration, hydrogen sulfide and carbon dioxide are liberated from the absorbent. Regeneration zone 110 is a distillation column operated under steam stripping conditions at a temperature of about 150° to 300° F. and a pressure of about 25 psia and contains a suitable number of distillation trays, which can be determined by one skilled in the art. The particular method or apparatus for regeneration is not critical to the present invention. It is not uncommon for heat stable salts to form in the regeneration zone as well as the absorption zone.

A regeneration overhead stream comprising carbon dioxide, hydrogen sulfide and water is discharged from regeneration zone 110 via line 16 and passed through a condenser 120 and then through a line 17 to a vessel 130. A tail gas stream comprising hydrogen sulfide and carbon dioxide is discharged from vessel 130 via line 18. A reflux stream comprising aqueous condensate of hydrogen sulfide and carbonic acid is discharged from vessel 130 via line 19. A portion of the reflux stream, typically less than 10 percent, preferably less than about 5 percent, and more preferably less than about 2 percent, is passed via line 20 to an electrodialysis zone 140, as hereinafter described. The reflux stream typically contains a total of from about 0.1 to 0.5 weight percent of carbon dioxide and hydrogen sulfide depending upon the operating conditions in the regeneration zone. Typically, the pH of the reflux stream is from about 3 to 6.

A regenerated solvent stream having substantially the same composition as the lean solvent stream and additionally comprising the heat stable salts is discharged from regeneration zone 110 via line 21. The concentration of heat stable salts in the regenerated solvent stream is typically from about 0.1 to 20 weight percent, often from about 1 to 12 weight percent. A portion of the regenerated solvent stream, typically less than about 10 percent, preferably less than about 5 percent, and more preferably less than about 2 percent, is passed to electrodialysis zone 140 as the feedstream via line 22. The remainder of the regenerated solvent stream is recycled to absorption zone 100 via line 11 as hereinbefore described. The pH of the regenerated solvent stream is typically from about 5 to 10.

Electrodialysis zone 140 comprises a cathode compartment, an anode compartment and about 50 repeat units wherein each repeat unit contains a reflux compartment ("R"), a product compartment ("P"), a feed compartment ("F"), and an acid compartment ("A"). Also illustrated in electrodialysis zone 140 are acid compartment ("A'") and a reflux compartment ("R''") from adjacent repeat units. Electrodialysis zone 140 contains cationic selective membranes ("C") and anionic selective membranes ("A") between the respective compartments. The temperature in electrodialysis zone 140 is maintained at about 90° to 130° F., often about 110° F. A direct current potential at a current density of about 15 to 50 amps per square foot, often about 30 amps per square foot of exposed membrane area, is passed transversely across each compartment in electrodialysis zone 140.

In the feed compartment F, amine cations dissociate from chloride anions. The amine cations permeate through the cationic selective membrane to the product compartment P. The chloride anions permeate through the anionic selective membrane to the acid compartment A. In the reflux compartment R, carbonate anions and hydrosulfide anions dissociate from hydrogen cations. The carbonate anions permeate through the anionic selective membrane to product compartment P. The hydrogen cations permeate through the cationic selective membrane to the adjacent acid compartment A'. Hydrogen cations present in adjacent reflux compartment R'' permeate through the cationic selective membrane into the acid compartment A. Water-containing streams are introduced to acid compartment A and product compartment P via lines 23 and 24, respectively, as carrier streams for the ions which permeate into such compartments.

A product stream containing the amine in salt form having carbonate anions and hydrosulfide anions associated therewith is discharged from product compartment P via line 14. Product stream 14 is combined with rich solvent stream 13 and introduced to regeneration zone 110 as feed as hereinbefore described. Alternatively, the product stream can be added directly to absorption zone 100, e.g., by combination with lean solvent stream 11.

An acid product stream comprising hydrochloric acid is discharged from the acid compartment A via line 26. Typically the concentration of hydrochloric acid in stream 26 will be from about 1 to 10 weight percent.

A feed effluent stream having essentially the same composition as feedstream 22, except for a reduced level of heat stable salts and heat regenerable salts, is discharged from feed compartment F via line 27. Feed effluent stream 27 can, for example, be combined with line 11 and passed to absorption zone 100 or recycled to the feed compartment for further removal of heat stable salts.

A reflux effluent stream having essentially the same composition as reflux stream 20, except for a lower carbonic acid and hydrogen sulfide content, is discharged from reflux compartment R via line 28. Reflux effluent stream 28 can, for example, be combined with line 14 and passed to regeneration zone 110 or recycled to the reflux compartment for further ion transfer or returned to regeneration zone 110 via line 25. Preferably, the flow rate of reflux stream 20 is sufficient to provide enough sulfide, hydrosulfide or carbonate anions to associate with the amine cations in product compartment P and also sufficient to inhibit the permeation of any amine cations which are present in reflux compartment R (small amounts of amine cations may permeate from product compartment P through the anionic selective membrane into reflux compartment R) into acid compartment A'.

Although the invention has been described with respect to specific aspects, those skilled in the art will recognize that other variations are possible within the scope of the claims which follow. For example, it may be desirable to utilize ion exchange resins in connection with the electrodialysis zone of the present invention in order to enhance the ion transfer, particularly in the aspect of the invention where the heat stable salts are converted to amine carbonate or hydrosulfide salts. In addition, those skilled in the art of electrodialysis know that electrode rinse solutions are often passed through the anode and cathode compartments to supply anions and cations for electrical conductivity. However, in the process of the present invention a portion of the reflux stream from the regeneration zone, containing, e.g., sulfurous acid, can advantageously be used for this purpose. Furthermore, although the electrodialysis zone generally provides regenerable amine salts, it is to be understood that, in the case of a diamine, the electrodialysis zone can provide an amine in salt form where either the first amine group or both the first and second amine groups have heat regenerable anions associated therewith in addition to amine salts wherein the first amine group is in a salt form and the second amine group is in free base form.

Moreover, when used in an acid gas absorption process, such as a sulfur dioxide absorption process, the electrodialysis zone of the present invention can be used as the primary regeneration means instead of steam stripping. In such a mode of operation, the rich solvent stream is passed to the feed compartment of the electrodialysis zone and a reflux stream, preferably containing carbonic acid, is passed to the reflux compartment. Thus, both heat stable anions, e.g., sulfate anions, and heat regenerable anions, e.g., sulfite anions, can be replaced with weaker heat regenerable anions, e.g., carbonate anions, to form a treated solvent stream which can be returned to the absorption zone as lean solvent. Also, in the case of a diamine, if the electrodialysis zone is operated to provide a product stream containing a diamine wherein the first amine group is in a salt form associated with an anion whose corresponding acid is a weaker acid than the acid gas being absorbed, then the product stream can be used to polish, or post-scrub, the effluent gas stream from the absorption process for further acid gas removal.

We claim:

1. A process for converting heat stable amine salts to heat regenerable amine salts which comprises:

(a) passing a feedstream comprising an amine in salt form having heat stable anions associated therewith to an electrodialysis zone having a cathode compartment, an anode compartment and at least one repeat unit comprising a reflux compartment disposed between the cathode compartment and the anode compartment, a product compartment disposed between the reflux compartment and the anode compartment, a feed compartment disposed between the product compartment and the anode compartment, and an acid compartment disposed between the feed compartment and the anode compartment, said feed stream being passed to the feed compartment;

(b) passing a reflux stream comprising a salt or acid of a heat regenerable anion to the reflux compartment;

(c) passing a direct current potential transversely across each compartment, said current being effective to cause: (1) amine cations to dissociated from the heat stable amine salts in the feed compartment and pass into the product compartment; (2) heat regenerable anions to dissociate from the salt or acid in the reflux compartment and pass into the product compartment; and (3) heat stable anions to dissociate from the heat stable amine salts in the feed compartment and pass into the acid compartment; and (d) discharging from the product compartment a product stream comprising an amine in salt form having regenerable anions associated therewith.

2. The process of claim 1 wherein, during said current passage, cations from a salt or acid of a heat regenerable anion from a reflux compartment of another repeat unit adjacent to said acid compartment pass into said acid compartment.

3. The process of claim 2 further comprising discharging from the acid compartment an acid stream comprising a salt or acid of the heat stable anion.

4. The process of claim 1 wherein the heat stable anion is selected from the group consisting of sulfate anions, thiosulfate anions, polythionate anions, thiocyanate anions, formate anions, halide anions, nitrate anions, nitrite anions, acetate anions, oxylate anions and mixtures thereof.

5. The process of claim 1 wherein the heat regenerable anion is selected from the group consisting of sulfite anions, sulfide anions, carbonate anions, hydrosulfide anions, and mixtures thereof.

6. The process of claim 1 wherein the feedstream further comprises water and the amine in free base form.

7. The process of claim 1 wherein the feedstream comprises from about 0.1 to 25 weight percent of the amine in salt form having heat stable anions associated therewith, from about 5 to 60 weight percent of the amine in free base form and from about 30 to 95 weight percent water.

8. The process of claim 1 wherein the amine is selected from the group consisting of alkanolamines, alkyleneamines, aromatic amines, heterocyclic amines and mixtures thereof.

9. The process of claim 1 wherein the salt of the heat regenerable anion is selected from the group consisting of alkali metal sulfites, alkali metal carbonates, alkaline earth metal sulfites, alkaline earth metal carbonates and alkali metal sulfide and hydrosulfides.

10. The process of claim 1 wherein the acid of the heat regenerable anion is selected from the group consisting of sulfurous acid, carbonic acid and hydrogen sulfide.

11. The process of claim 1 wherein the salt of the heat stable anion is selected from the group consisting of alkali metal sulfates, alkali metal halides, alkaline earth metal sulfates, alkaline earth metal halides, alkali metal nitrates and nitrites, alkaline earth metal nitrates and nitrites, and mixtures thereof.

12. The process of claim 1 wherein the acid of the heat stable anion is selected from sulfuric acid, hydrochloric acid, hydrofluoric acid, nitric acid, nitrous acid, acetic acid and mixtures thereof.

13. The process of claim 1 further comprising passing an aqueous carrier stream to at least one of the product compartment and the acid compartment.

14. The process of claim 1 further comprising discharging a feed effluent stream from the feed compartment and recycling at least a portion of the feed effluent stream to the feed compartment.

15. The process of claim 1 further comprising discharging a reflux effluent stream from the reflux compartment and recycling at least a portion of the reflux effluent stream to the reflux compartment.

16. A process for converting heat stable amine salts to heat regenerable amine salts which comprises:
  (a) passing a feedstream comprising an amine in salt form having sulfate anions associated therewith to an electrodialysis zone having a cathode compartment, an anode compartment and at least one repeat unit comprising a reflux compartment disposed between the cathode compartment and the anode compartment, a product compartment disposed between the reflux compartment and the anode compartment, a feed compartment disposed between the product compartment and the anode compartment, and an acid compartment disposed between the feed compartment and the anode compartment, said regenerated solvent stream being passed to the feed compartment;
  (b) passing a reflux stream comprising a salt or acid of a sulfite anion to the reflux compartment;
  (c) passing a direct current potential transversely across each compartment, said current being effective to cause: (1) amine cations to dissociate from the heat stable amine salts in the feed compartment and pass into the product compartment; (2) sulfite anions to dissociate from the salt or acid in the reflux compartment and pass into the product compartment; and (3) sulfate anions to dissociate from the heat stable amine salts in the feed compartment and pass into the acid compartment; and
  (d) discharging from the product compartment a product stream comprising an amine in salt form having sulfite anions associated therewith.

17. The process of claim 16 wherein, during said current passage, cations from a salt or acid of a sulfite anion from a reflux compartment of another repeat unit adjacent to said acid compartment pass into said acid compartment.

18. The process of claim 17 further comprising discharging from the acid compartment an acid stream comprising a salt or acid of the sulfate anion.

* * * * *